(12) United States Patent
Berndorfer

(10) Patent No.: US 12,734,303 B2
(45) Date of Patent: Sep. 15, 2026

(54) SWITCH ASSEMBLY FOR AN ELECTRONIC SYSTEM OF A DRUG DELIVERY DEVICE

(71) Applicant: Sanofi, Paris (FR)

(72) Inventor: Roman Immo Berndorfer, Walldorf (DE)

(73) Assignee: SANOFI, Paris (FR)

( * ) Notice: Subject to any disclaimer, the term of this patent is extended or adjusted under 35 U.S.C. 154(b) by 827 days.

(21) Appl. No.: 17/914,501

(22) PCT Filed: Mar. 25, 2021

(86) PCT No.: PCT/EP2021/057667
§ 371 (c)(1),
(2) Date: Sep. 26, 2022

(87) PCT Pub. No.: WO2021/191324
PCT Pub. Date: Sep. 30, 2021

(65) Prior Publication Data

US 2023/0125718 A1 Apr. 27, 2023

(30) Foreign Application Priority Data

Mar. 27, 2020 (EP) .................................... 20315066
Nov. 16, 2020 (EP) .................................... 20315451
Jan. 4, 2021 (EP) .................................... 21315001

(51) Int. Cl.
*A61M 5/315* (2006.01)
*A61M 5/178* (2006.01)

(52) U.S. Cl.
CPC ...... *A61M 5/31551* (2013.01); *A61M 5/1782* (2013.01); *A61M 5/31568* (2013.01);
(Continued)

(58) Field of Classification Search
CPC ........... A61M 5/31551; A61M 5/1782; A61M 5/31568; A61M 5/3157; A61M 5/31585;
(Continued)

(56) References Cited

U.S. PATENT DOCUMENTS 6,236,002 B1 5/2001 Chou
2016/0015903 A1* 1/2016 Madsen ........... A61M 5/31568 604/211
(Continued)

FOREIGN PATENT DOCUMENTS

CN 102458535 A 5/2012
CN 105073165 A 11/2015
(Continued)

OTHER PUBLICATIONS

Notice of Reasons for Refusal, JP Patent Application No. 2022-558021, dated Nov. 12, 2024, pp. 1-14 (with pp. 1-7 being an English translation).
(Continued)

*Primary Examiner* — Tasnim Mehjabin Ahmed
(74) *Attorney, Agent, or Firm* — Bond, Schoeneck & King, PLLC

(57) ABSTRACT

The present disclosure refers to a switch assembly for an electronic system of a drug delivery device. The switch assembly includes a chassis supporting a PCBA including at least a first electrical contact, a second electrical contact, a third electrical contact and a fourth electrical contact and a ring with a ratchet profile. The chassis moves axially relative to the ring from a first axial position to a second axial position during a first switch operation mode. The chassis and the ring are configured such that the ring rotates relative to the chassis during a second switch operation mode. The first electrical contact and the second electrical contact are arranged such that upon axial movement of the chassis
(Continued)

towards the ring during the first switch operation mode, an electrical connection between the first electrical contact and the second electrical contact is closed.

13 Claims, 5 Drawing Sheets

(52) U.S. Cl.
CPC ...... *A61M 5/3157* (2013.01); *A61M 5/31585* (2013.01); *A61M 2205/3317* (2013.01); *A61M 2205/35* (2013.01)

(58) Field of Classification Search
CPC ...... A61M 2205/3317; A61M 2205/33; A61M 2205/35; A61M 2205/3561; A61M 2205/8212
See application file for complete search history.

(56) References Cited

U.S. PATENT DOCUMENTS

| | | | | |
|---|---|---|---|---|
| 2020/0078527 | A1 | 3/2020 | Biederman et al. | |
| 2021/0146061 | A1* | 5/2021 | Byerly | A61M 5/31551 |

FOREIGN PATENT DOCUMENTS

| | | | |
|---|---|---|---|
| CN | 105764550 | A | 7/2016 |
| CN | 108472454 | A | 8/2018 |
| EP | 2729202 | | 5/2018 |
| EP | 2890435 | | 3/2020 |
| EP | 20315066.9 | | 3/2020 |
| EP | 20315357.2 | | 7/2020 |
| JP | 2016514249 | A | 5/2016 |
| JP | 2018515232 | A | 6/2018 |
| WO | 2013010887 | A1 | 1/2013 |
| WO | WO 2014/033195 | | 3/2014 |
| WO | 2018013419 | A1 | 1/2018 |
| WO | 2019040117 | A1 | 2/2019 |
| WO | WO 2019/040313 | | 2/2019 |
| WO | 2019121448 | A1 | 6/2019 |
| WO | 2019164936 | A1 | 8/2019 |
| WO | WO 2019/164936 | | 8/2019 |
| WO | WO 2019/173097 | | 9/2019 |
| WO | 2020035406 | A1 | 2/2020 |
| WO | WO 2021/191327 | | 9/2021 |

OTHER PUBLICATIONS

Notice of Reasons for Refusal, JP Patent Application No. 2022-558021, dated Sep. 10, 2024, pp. 1-14 (with pp. 1-7 being an English translation).

International Preliminary Report on Patentability in International Appln. No. PCT/EP2021/057667, mailed on Oct. 6, 2022, 9 pages.

International Search Report and Written Opinion in International Appln. No. PCT/EP2021/057667, mailed on May 26, 2021, 12 pages.

First Office Action, CN Application No. 202180023184.1, dated Feb. 21, 2025, pp. 1-22 (with pp. 1-9 being a translation).

* cited by examiner 12
11
13
1
10
14
15
16
17
18 motion sensing unit
120
100
110
130
electrical power supply
electronic control unit
use detection unit
150
communication unit
140

SWITCH ASSEMBLY FOR AN ELECTRONIC SYSTEM OF A DRUG DELIVERY DEVICE

CROSS REFERENCE TO RELATED APPLICATIONS

The present application is the national stage entry of International Patent Application No. PCT/EP2021/057667, filed on Mar. 25, 2021, and claims priority to Application Nos. EP 20315066.9, filed on Mar. 27, 2020; EP 20315451.3, filed on Nov. 16, 2020; and EP 21315001.4, filed on Jan. 4, 2021, the disclosures of which are incorporated herein by reference.

TECHNICAL FIELD

The present disclosure is generally directed to an electronic system for a drug delivery device. The present disclosure further relates to a drug delivery device, which preferably comprises the electronic system.

BACKGROUND

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges.

Rather, the pre-filled cartridges may not be removed and replaced from these devices without destroying the device itself. Consequently, such disposable devices need not have a resettable dose setting mechanism. The present disclosure is applicable for disposable and reusable devices.

For such devices the functionality of recording doses that are dialled and delivered from the pen may be of value to a wide variety of device users as a memory aid or to support detailed logging of dose history. Thus, drug delivery devices using electronics are becoming increasingly popular in the pharmaceutical industry as well as for users or patients. For example, a drug delivery device is known from EP 2 729 202 B1 comprising an electronically controlled capturing system for capturing data related to the amount of drug expelled from a reservoir by expelling means.

However, especially if the device is designed to be self-contained, that is to say without a connector for a connection to an electrical power source which is necessary to provide electrical power for the operation of the device, the management of the resources of a power supply integrated into the device is particularly important.

Unpublished EP20315066.9 and EP20315357.2 disclose advantageous embodiments of electronic systems for drug delivery devices with improved power management. These electronic systems comprise a switch assembly for activating/deactivating power consuming functions of the electronic systems.

An alternative rotary encoder comprising several electrical switches which are selectively opened and closed by means of a mechanical wave generator in the form of a profile having valleys and ridges engaging and actuating the switches is known from WO 2019/173097 A1.

Such drug delivery devices are typically manufactured in large scale such that an efficient and simple assembly is an important issue to keep production costs reasonably low.

SUMMARY

The present disclosure relates to drug delivery devices comprising an electronic system or electronic systems for drug delivery devices allowing reliable activation/deactivation of functions of the electronic system as well as an efficient assembly.

One aspect of the disclosure relates to a switch assembly for an electronic system of a drug delivery device. The switch assembly comprises a chassis supporting a Printed Circuit Board Assembly (PCBA) which has a distal surface comprising at least a first electrical contact, a second electrical contact, a third electrical contact and a fourth electrical contact. The switch assembly further comprises a ring, e.g. an encoder ring of a rotary sensor, comprising a ratchet profile. The ratchet profile may comprise bottom sections and peak sections, e.g. arranged facing radially inwards of the ring. Preferably, the chassis and the ring are arranged and adapted such that the chassis moves axially relative to the ring from a first, e.g. more distant, axial position to a second, e.g. closer, axial position during a first switch operation mode, e.g. during the transition from the dose setting operation to the dose delivery operation of the drug delivery device or when the chassis is pressed in a 0U dialled condition of the drug delivery device. Further, the chassis and the ring are configured such that the ring rotates relative to the chassis during a second switch operation mode, e.g. during the dose delivery operation of the drug delivery device. A reliable switching in both switching modes may be obtained if the first electrical contact and the second electrical contact are arranged such that upon axial movement of the chassis towards the ring during the first switch operation mode an electrical connection between the first electrical contact and the second electrical contact is closed. In addition, an elastically deformable arm may be radially interposed between ratchet profile of the ring and the chassis. Preferably, the arm axially and rotationally constrained to the chassis and is guided on the ratchet profile such that the arm at least during the second switch operation mode elastically deforms in a radial direction towards the chassis thereby alternately opening and closing an electrical connection between the third electrical contact and the fourth electrical contact via the arm.

This arrangement of the switch assembly has the further advantage that the chassis, the PCBA with its contacts at the distal surface, the ring and the contacts may be mounted from the same direction into each other to form the switch assembly. This significantly increases assembly efficiency compared with alternatives requiring mounting of the component parts from different directions. In addition, the number of additional component parts required to build the switch assembly is relatively low. For example, in drug delivery devices with an electronic system comprising the ring, the chassis and the PCBA, it is only required to provide a metal component comprising the arm. Thus, it is only required to modify the ring and the PCBA to provide the switch assembly according to the present disclosure. The low number of additional component parts contributes in making the assembly process highly efficient.

According to a further independent aspect of the present disclosure, a rounded piece of metal is provided which is scalable in diameter, thickness and height and, thus, is adjustable to various medication pens and/or their respective connectivity modules, which has one or more spring elements built in. During rotational movement of either parts of the pen and/or the connectivity module the spring element may interact with respective counterpart. According to this aspect of the disclosure, the rounded metal part can either be fixed or rotate, subsequently the counterpart can either rotate or be fixed. The overall force to rotate the rotational part of the application versus the fixed part can be adjusted by selecting the spring accordingly. This aspect of the disclosure is based on the idea that if the spring element interacts with a counterpart, the spring is reversibly bent which can be used as a trigger signal e.g. by closing or opening an electrical contact. The rotational movement between the spring element and counterpart can be used in both directions. As a further benefit, the relative rotational movement between two parts can be used to generate a tactile and/or audible patient feedback signal.

In the switch assembly, the arm may comprise at least one detent or protrusion adapted to engage the ratchet profile of the ring. In more detail, the detent or protrusion may fit into the bottom sections of the ratchet profile and may be able to slide over the peak sections of the ratchet profile upon relative rotation of the ring with respect to the chassis and the arm. The ratchet profile and the detent may be adapted to each other to permit relative rotation in only one direction whereas blocking relative rotation in the opposite direction. As an alternative, the ratchet profile and the detent may permit relative rotation in both directions.

The mounting of the switch assembly may be facilitated if the arm is part of a substantially annular conductive spring member which is biased into abutment with the ratchet profile of the ring and which can be at least partially deflected radially inwards into an annular space between the ring and the chassis. For example, the spring member may be a slotted ring which is clamped into the space between the ring and the chassis by elastically widening or elastically constraining the spring member.

A rotary switch of the switch assembly may be established in a simple and reliable manner if the third electrical contact and the fourth electrical contact are provided on a flexible flap or a flexboard section of the PCBA which extends distally from the PCBA to a position between the ring and the chassis. In other words, the third and fourth contact may be arranged next to each other on the flap or flexboard section such that contact of the flap or flexboard section with the arm electrically bridges and connects the third electrical contact and the fourth electrical contact. For example, the arm may alternate between contacting bottom sections and peak sections of the ratchet profile and thereby elastically deflects to connect with and disconnect from the third electrical contact and the fourth electrical contact during the second switch operation mode.

An axial switch of the switch assembly may comprise the first electrical contact which may be a first lever having one end attached to the PCBA and an opposite free end, and the second electrical contact which may be a second lever having one end attached to the PCBA and an opposite free end. For example, the free ends of the levers are arranged such that upon axial movement of the chassis towards the ring during the first switch operation mode an electrical connection between the first electrical contact and the second electrical contact is closed by deflecting at least the first lever with respect to the second lever. In more detail, the first lever may extend through the chassis with its free end protruding out of the chassis into a position in which upon axial movement of the chassis towards the ring during the first switch operation mode the ring or a component part connected to the ring, e.g. a portion of a dial assembly, deflects the first lever. In this example, the first lever and the second lever may be located in a space formed in the chassis radially inside the ring.

As an alternative, an axial switch of the switch assembly may further comprise a housing and a dial grip or dose knob. For example, axial movement of the chassis towards the ring during the first switch operation mode may be caused by axial displacement of at least a portion of the dial grip or dose knob with respect to the housing which closes a gap between the first electrical contact and the second electrical contact. In this example, the first electrical contact and the second electrical contact may be arranged on a proximal side of the PCBA facing away from the ring.

According to a further aspect of the present disclosure a method for assembling a drug delivery device is provided, the drug delivery device comprising a dose setting and drive mechanism, an electronic system with a switch assembly comprising the chassis, the PCBA with its contacts at the distal surface, the ring with the annular ratchet profile and the first and second electrically conductive arms, wherein these component parts of the drug delivery device are mounted from one single direction into and/or onto each other, preferably mounted from a proximal button end of the drug delivery device towards a distal dispensing end. Some of these component parts may be mounted as a pre-assembled sub-unit which itself may or may not be mounted from the same single direction.

The examples of the switch assemblies are especially applicable in drug delivery devices comprising an electronic system. The present disclosure is applicable for devices which are manually driven, e.g. by a user applying a force to an injection button, for devices which are driven by a spring or the like and for devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

According to one aspect of the present disclosure, a drug delivery device may comprise an electronic system with the switch assembly as described above. For example, the drug delivery device may comprise a dose setting and drive mechanism and a button module. In more detail, the dose setting and drive mechanism may be configured to perform a dose setting operation for setting a dose to be delivered by the drug delivery device and a dose delivery operation for delivering the set dose. Preferably, the dose setting and drive mechanism comprises the ring of the switch assembly. Further, the button module may comprise an electronic control unit on the PCBA, a rotary sensor, e.g. with a light source and a corresponding optical sensor, a communication unit with a wireless communication interface for communicating with another device, and a use detection unit comprising the switch assembly. Preferably, the electronic control unit is configured to control an operation of the electronic system.

According to a further aspect of the present disclosure, the button module and the dose setting and drive mechanism may be configured such that the dose dial assembly rotates relative to the button module during the dose delivery operation but does not rotate relative to the button module during the dose setting operation and that the button module moves axially relative to the dose dial assembly during the transition from the dose setting operation to the dose delivery operation, or when the button module is pressed in a 0U dialled condition.

According to a further aspect of the present disclosure, the electronic system is configured such that the communication unit is switched from a sleeping mode into an operation mode inducing the communication unit to initiate a manual synchronisation and/or a pairing with another device upon closing an electrical connection between the first electrical contact and the second electrical contact during the first switch operation mode. In addition or as an alternative, the electronic system is configured such that the rotary sensor is switched from a sleeping mode into an operation mode inducing the rotary sensor to initiate a motion detection upon closing an electrical connection between the second electrical contact and the third electrical contact via the arm during the second switch operation mode.

The present disclosure provides advantageous embodiments relating to the integration of mechanically activated electronic switches to initiate different device functions. The at least one switch assembly may form or may be part of a use detection unit of the electronic system. Such a use detection unit may comprise the use of a rotationally activated electronic switch (rotary switch) to wake an electronic encoding module attached to an injection device and/or the use of an axially activated electronic switch (axial switch) to initiate pairing functionality of an encoding module, e.g. a rotary sensor, attached to an injection device, with another smart electronic device. A mechanically activated electronic switch may be or may form part of an electrical use detection unit operatively connected to an electronic control unit. The electrical use detection unit may be configured to generate a first signal which is indicative that the user has commenced or finished the relative movement between the dose setting and drive mechanism and the button module. Thus, the present disclosure permits an injection device to maintain a low power state when energising of the encoding sensor(s) or pairing is not required, but to wake when either functionality is required. This is especially applicable to devices where a module rotates relative to an axially adjacent mechanism component during dose delivery but does not rotate relative to that component during dialing and/or to devices where the module moves axially relative to an adjacent mechanism component during the transition from a dialling to a dispensing state, or when the button module is pressed in a 0U dialled condition, i.e. a state at the completion of dose dispensing and prior to selecting a new dose.

According to one aspect of the present disclosure an electronic system comprises a dose setting and drive mechanism which is configured to perform a dose setting operation for setting a dose to be delivered by the drug delivery device and a dose delivery operation for delivering the set dose. The dose setting and drive mechanism comprises at least a ring which may be, preferably indirectly, operable by a user during the dose setting operation and/or the dose delivery operation. For example, the dose setting and drive mechanism may comprise one or more of the following components: a dial grip, a dial or display member (e.g. a number sleeve), a driver, a clutch, a piston rod, an inner and/or outer housing component. The dose setting and drive mechanism of the present disclosure may be based on the dose setting and drive mechanism disclosed in EP 2 890 435.

According to a further aspect of the present disclosure an electronic system comprises a button module comprising at least an electronic control unit, e.g. consisting of or comprising a PCBA, being configured to control an operation of the electronic system. The button module may be permanently or detachably attached to a trigger, a button or a dial grip, e.g. at or near the proximal end of the drug delivery device. The button module and/or the electronic control unit may have a distal surface facing towards the dose setting and drive mechanism, for example for providing an interface for mechanical interaction and/or electrical connection with further component parts of the system.

In one embodiment, the electronic system has a first state and a second state. The first state and the second state may be different states of operation of the electronic system. The electronic control unit may have at least a first, preferably low power consumption, state and a second, preferably high power consumption, state. In the first state, the system may be in an idle state, where the system could not operate with the desired functionality assigned to the electronic system, e.g. use detection, motion detection, encoding, synchronisation and/or pairing. In other words, at least one function may be not activated in this first state. In the second state, the system may be ready to operate with the desired functionality, e.g. when the system is triggered to start an operation and/or when in the second state a dose setting operation and/or a dose delivery operation is being performed. The electronic system may have an increased electrical power consumption in the second state as compared to the first state. For example, in the second state, one or more electrical or electronic units of the electronic system may be switched to a state of higher power consumption, e.g. an on state, as compared to the first state, where the respective unit may be in a sleep state with low power consumption or an off state with no power consumption at all, e.g. because the connection to an electrical power supply is interrupted. For example, a communication unit and/or an encoding module. e.g. a rotary sensor, may be activated in this second state.

An encoding module or unit is typically suitable to detect a motion of a specific component part of the dose setting and drive mechanism and to generate signals indicative of the amount of motion of this component part. For example, the encoding module or unit may detect rotational movement of an encoder ring attached to a dial sleeve, which encoder ring is preferably the ring of the switch assembly, during the dose setting operation and/or during the dose delivery operation. According to one aspect of the present disclosure, the encoding module comprises a rotary sensor for detection of a rotational movement. A rotary sensor may comprise a light source with a corresponding optical sensor, preferably two light sources with two corresponding optical sensors, for detecting a rotational movement of a component part having a pattern. As an alternative, a rotary sensor may use other detection techniques, e.g. the rotary sensor may comprise an electrical sliding contact, a mechanical switching arrangement and/or a magnetic sensor.

For example, the encoder ring may further comprise a pattern provided at least on its outer surface which can be detected by the rotary sensor. According to one aspect, the rotary sensor comprises a primary sensor and secondary sensor which are configured to target specially adapted regions at the proximal end of the dial sleeve, e.g. at the encoder ring. In this example, the primary sensor and the secondary sensor may be light reflective sensors. Therefore, the specially adapted proximal regions of the dial sleeve or the encoder ring may be divided into at least one reflective area and at least one non-reflective (or absorbent) area. The rotary sensor may be an optical sensor emitting light from an LED whose light is reflected by the reflective region(s) of the encoder ring and the sensor detects the reflected light. The sensor then converts the detected light to an electrical output. The encoding or motion sensing unit may comprise one or more of such optical rotary sensor(s), for example two optical rotary sensors located circumferentially spaced about the encoder ring.

The electronic system may further comprise an encoding or motion sensing unit which is in a sleeping mode in the first low power consumption state and which is activated in the second high power consumption state, and/or a communication unit for communicating with another device, which communication unit is in a sleeping mode in the first low power consumption state and which is activated in the second high power consumption state. In an exemplary embodiment of the present disclosure, the electronic system may comprise an encoding or motion sensing unit and a communication unit wherein both units may be independently activated or in a sleeping mode. Thus, there may be more than two power consumption states, namely a state where both units are deactivated or in a sleeping mode, a state where only the encoding or motion sensing unit is activated, a state where only the communication unit is activated and a state where both units are activated. The power consumption of the electronic system may be different for each of these four states. Nevertheless, only a first low power consumption state and a second high power consumption state are discussed herein for simplification reasons.

In an embodiment, the electronic system may be suitable to collect or measure dose data, e.g. corresponding to the set dose or the dispensed dose, using the encoding or motion sensing unit. Such dose data may be collected only in the second state of the system. In one embodiment, the encoding or motion sensing unit, when it is active, may be operable to gather motion data or measurement data relating to the movement of e.g. a dial member, a driver and/or a piston rod. The electronic control unit may be configured to convert this data into dose data, e.g. characteristic for the size of the dose which has been set or has been delivered in the respective operation. The encoding or motion sensing unit may be designed as described in unpublished EP20315066.9 and EP20315357.2 the disclosure of which is incorporated herein by reference.

The communication unit may comprise a wireless communication interface for communicating with another device, wherein the electronic system is configured such that it is switched from the first state into the second state by the electronic control unit in response to the first signal, thereby inducing the communication unit to initiate a manual synchronisation and/or a pairing with another device.

The electronic control unit may, in response to reception of the first signal issue a command, e.g. a signal, to another unit of the electronic system such that this unit is switched on or rendered operational. This unit may be the communication unit for communicating with another device, e.g. a wireless communications interface for communicating with another device via a wireless network such as Wi-Fi or Bluetooth®, or even an interface for a wired communications link, such as a socket for receiving a Universal Series Bus (USB), mini-USB or micro-USB connector. Preferably, the electronic system comprises an RF, WiFi and/or Bluetooth unit as the communication unit. The communication unit may be provided as a communication interface between the system or the drug delivery device and the exterior, such as other electronic devices, e.g. mobile phones, personal computers, laptops and so on. For example, dose data may be transmitted by the communication unit to the external device. The dose data may be used for a dose log or dose history established in the external device.

In one embodiment, the communication unit comprises a wireless communication interface for communicating with another device, wherein the electronic system is configured such that it is switched from the first state into the second state by the electronic control unit in response to the first signal of the at least one switch of the use detection unit, thereby inducing the communication unit to initiate a manual synchronisation and/or a pairing with another device or to initiate a mode for amending the settings of the electronic system.

According to one aspect of the present disclosure an electronic system comprises a dose setting and drive mechanism, an electrical power supply, e.g. a rechargeable or non-rechargeable battery, an electronic control unit, an electrical use detection unit and an encoding or motion sensing unit and/or a communication unit for communicating with another device.

In one embodiment, the device or the electronic system comprises an electronic control unit, e.g. comprising a microprocessor or microcontroller. The electronic control unit may be configured to control operation of the drug delivery device or the electronic system. The electronic control unit may be arranged on a conductor carrier and electrically conductively connected with conductors on the conductor carrier. The conductor carrier may be a circuit board such as a printed circuit board. The conductor carrier may be retained in the interior of the user interface member of the system or the device. The power supply may be arranged in the interior of the electronic system such as in the interior of the user interface member.

According to one aspect of the present disclosure, the electronic system is applicable to limit the battery capacity requirement of an injection device, where it is advantageous to be able to have the device in a low power state when any electronic functionality is not required. This can be achieved by mechanical switches which are activated by relative motion between the electronic button module and adjacent components as required, e.g. the above exemplarily mentioned encoder ring as part of the dial sleeve assembly.

According to one aspect of the present disclosure, the functionality of a manual synchronization is to be initiated on pressing the button module, when the device is at 0U dialled. When the button module is pressed, in any device state, the button module is translated, e.g. together with a clutch, distally relative to the dial sleeve assembly. The nominal axial travel may be limited, e.g. to less than 3 mm, for example to between 1.5 mm and 2.0 mm, travel of the button module relative to the dial sleeve (and the encoder ring), further relative axial motion is limited. The axial switch of one embodiment of the use detection unit is mounted in the underside of the button module and utilises the relative axial displacement between button module and dial sleeve assembly to trigger. The duration for which the button module is held in a depressed state may be used to allow multiple different functionalities to be initiated by the same switch, e.g. manual synchronisation for a short duration press and release, or pairing for a longer duration press and release.

According to one further aspect of the present disclosure, the functionality of e.g. encoding may be required to be initiated only when the device is dispensing. For example, in the device disclosed in EP 2 890 435, during dose setting the dial sleeve assembly, e.g. consisting of a dial sleeve and the encoder ring, and the button module extend (translate) helically from the device. Therefore, there is no relative rotation between the button module and the dial sleeve assembly during dose setting. To initiate dose delivery the button module, e.g. and a clutch, are translated distally relative to the device housing. After the clutch has translated a predefined distance, e.g. less than 2.0 mm, for example nominally 1.20 mm, the clutch disengages from the dial sleeve and the delivery mechanism enters the dispensing (dose delivery) mode. In this dispensing mode the dial sleeve assembly retracts along the helical path into the device, whereas the button module does not rotate and only retracts with axial motion, until the 0U stop is engaged and dispense is complete. Thereby there is relative rotation of the button module with respect to the dial sleeve assembly during dispense. In the exemplary embodiment of a rotational switch of the use detection unit, this rotational switch may be mounted in the underside of the button module and utilises the relative rotation between the button module and dial sleeve assembly to trigger.

In this exemplary application to the device disclosed in EP 2 890 435, the axial switch will also be triggered when the button module is pressed as part of a dispensing event. However, with the embodiment described the relative order of the rotational and axial switch state changes cannot be guaranteed. It is possible that the axial switch will not be triggered before the point of clutch disengagement, e.g. 1.2 mm button module translation, so some rotation of the dial sleeve assembly could occur prior to the axial switch state change. Use of the rotational switch to initiate e.g. an optical encoding system ensures that the delivered dose is accurately recorded, irrespective of the axial position of the button module. Without the requirement to trigger prior to clutch disengagement, the maximum deflection of the axial switch contacts and therefore the forces, stresses and package space of this axial switch can be minimised.

According to a further aspect of the present disclosure, the use detection unit comprises the axial switch and the rotational switch wherein the electronic control unit is adapted to switch the encoding or motion sensing unit into its low power consumption state in response to a signal that the axial switch is switched from its first electrical state, e.g. an electrically open circuit, into its second electrical state, e.g. an electrically closed circuit. In more detail, when the user releases the button module at the end of dispense (or midway through a dispense event) the button module and clutch translate proximally relative to the device, e.g. under a clutch spring force. The axial switch state will change during this motion, but the rotational switch state will not. The change of state of the axial switch following a dispense event, provides information to the controller (electronic control unit) that the user has released the button module. Without this information, an increased delay period would be required prior to a readout of the dispensed dose being displayed, since the system must wait to check for no further rotational switch signals to determine if the dose is complete. This would have a negative implication on battery life and user experience. Thus, although the use detection unit may comprise only the axial switch or only the rotational switch, a combination of the axial switch and the rotational switch provides additional benefits exceeding the possibility of triggering two different functions with two different switches.

The present disclosure further pertains to a drug delivery device comprising the electronic system as described above. The drug delivery device may comprise a container receptacle which is releasably attached to the dose setting and drive mechanism. As an alternative, the container receptacle may be permanently attached to the dose setting and drive mechanism. The container receptacle is adapted to receive a container, e.g. a cartridge, containing a medicament.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids. Optionally, one or more amino acids occurring in the naturally occurring peptide may have been deleted and/or replaced by other amino acids, including non-codeable amino acids, or amino acids, including non-codeable, have been added to the naturally occurring peptide. Examples of insulin analogues are Gly(A21), Arg(B31), Arg(B32) human insulin (insulin glargine); Lys(B3), Glu(B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C (Efpeglenatide), HM-15211, CM-3, GLP-1 Eligen, ORMD-0901, NN-9423, NN-9709, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, ZP-DI-70, TT-401 (Pegapamodtide), BHM-034. MOD-6030, CAM-2036, DA-15864, ARI-2651, ARI-2255, Tirzepatide (LY3298176), Bamadutide (SAR425899), Exenatide-XTEN and Glucagon-Xten.

An example of an oligonucleotide is, for example: mipomersen sodium (Kynamro®), a cholesterol-reducing antisense therapeutic for the treatment of familial hypercholesterolemia or RG012 for the treatment of Alport syndrome.

Examples of DPP4 inhibitors are Linagliptin, Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present invention include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present invention, which encompass such modifications and any and all equivalents thereof. An example drug delivery device may involve a needle-based injection system as described in Table 1 of section 5.2 of ISO 11608-1:2014(E). As described in ISO 11608-1:2014(E), needle-based injection systems may be broadly distinguished into multi-dose container systems and single-dose (with partial or full evacuation) container systems. The container may be a replaceable container or an integrated non-replaceable container.

As further described in ISO 11608-1:2014(E), a multi-dose container system may involve a needle-based injection device with a replaceable container. In such a system, each container holds multiple doses, the size of which may be fixed or variable (pre-set by the user). Another multi-dose container system may involve a needle-based injection device with an integrated non-replaceable container. In such a system, each container holds multiple doses, the size of which may be fixed or variable (pre-set by the user).

As further described in ISO 11608-1:2014(E), a single-dose container system may involve a needle-based injection device with a replaceable container. In one example for such a system, each container holds a single dose, whereby the entire deliverable volume is expelled (full evacuation). In a further example, each container holds a single dose, whereby a portion of the deliverable volume is expelled (partial evacuation). As also described in ISO 11608-1:2014 (E), a single-dose container system may involve a needle-based injection device with an integrated non-replaceable container. In one example for such a system, each container holds a single dose, whereby the entire deliverable volume is expelled (full evacuation). In a further example, each container holds a single dose, whereby a portion of the deliverable volume is expelled (partial evacuation).

The terms "axial", "radial", or "circumferential" as used herein may be used with respect to a main longitudinal axis of the device, the cartridge, the housing or the cartridge holder, e.g. the axis which extends through the proximal and distal ends of the cartridge, the cartridge holder or the drug delivery device.

The disclosure is not restricted to the subject matter defined in the appended claims. Rather, the disclosure may comprise improvements in addition or as an alternative to the ones defined in the independent claims as will be apparent from the description herein.

BRIEF DESCRIPTION OF THE FIGURES

Non-limiting, exemplary embodiments of the disclosure will now be described with reference to the accompanying drawings, in which.

DETAILED DESCRIPTION

Figures 1, 4:
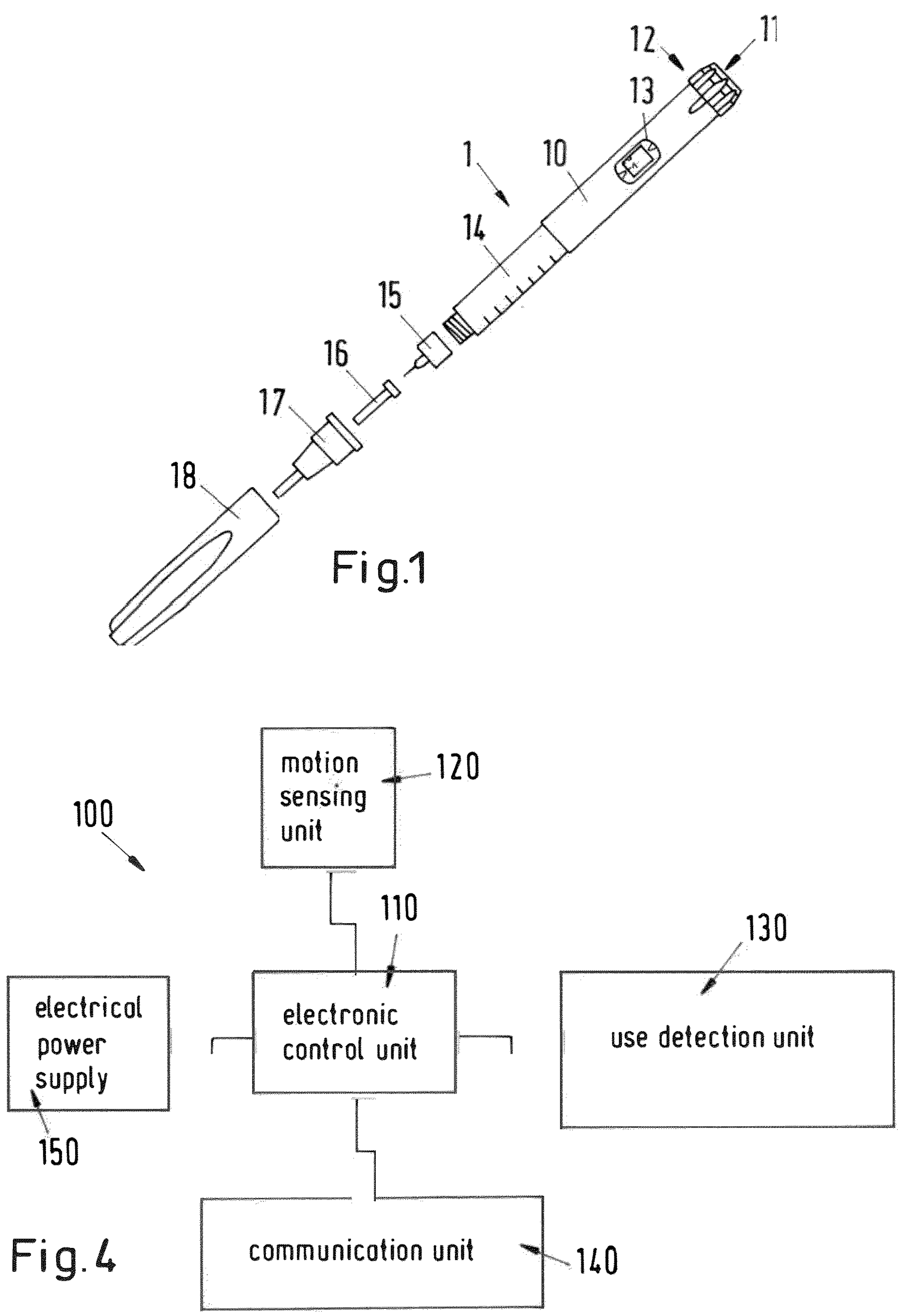
FIG. 1 shows an embodiment of a drug delivery device.
FIG. 4 illustrates schematically an embodiment of an electronic system for a drug delivery device.

In the figures, identical elements, identically acting elements or elements of the same kind may be provided with the same reference numerals.

In the following, some embodiments will be described with reference to an insulin injection device. The present disclosure is however not limited to such application and may equally well be deployed with injection devices that are configured to eject other medicaments or drug delivery devices in general, preferably pen-type devices and/or injection devices.

Embodiments are provided in relation to injection devices, in particular to variable dose injection devices, which record and/or track data on doses delivered thereby. These data may include the size of the selected dose and/or the size of the actually delivered dose, the time and date of administration, the duration of the administration and the like. Features described herein include the arrangement of sensing elements and power management techniques (e.g. to facilitate small batteries and/or to enable efficient power usage).

Certain embodiments in this document are illustrated with respect to the injection device disclosed in EP 2 890 435 where an injection button and grip (dose setting member or dose setter) are combined. The injection button may provide the user interface member for initiating and/or performing a dose delivery operation of the drug delivery device. The grip or knob may provide the user interface member for initiating and/or performing a dose setting operation. These devices are of the dial extension type, i.e. their length increases during dose setting. Other injection devices with the same kinematical behaviour of the dial extension and button during dose setting and dose expelling operational mode are known as, for example, the Kwikpen® device marketed by Eli Lilly and the Novopen® 4 device marketed by Novo Nordisk. An application of the general principles to these devices therefore appears straightforward and further explanations will be omitted. However, the general principles of the present disclosure are not limited to that kinematical behaviour. Certain other embodiments may be conceived for application to Sanofi's SoloSTAR® injection device where there are separate injection button and grip components/dose setting members. Thus, there may be two separate user interface members, one for the dose setting operation and one for the dose delivery operation.

"Distal" is used herein to specify directions, ends or surfaces which are arranged or are to be arranged to face or point towards a dispensing end of the drug delivery device or components thereof and/or point away from, are to be arranged to face away from or face away from the proximal end. On the other hand, "proximal" is used to specify directions, ends or surfaces which are arranged or are to be arranged to face away from or point away from the dispensing end and/or from the distal end of the drug delivery device or components thereof. The distal end may be the end closest to the dispensing and/or furthest away from the proximal end and the proximal end may be the end furthest away from the dispensing end. A proximal surface may face away from the distal end and/or towards the proximal end. A distal surface may face towards the distal end and/or away from the proximal end. The dispensing end may be the needle end where a needle unit is or is to be mounted to the device, for example.

FIG. 1 is an exploded view of a medicament delivery device or drug delivery device. In this example, the medicament delivery device is an injection device 1, e.g. a pen-type injector, such an injection pen disclosed in EP 2 890 435.

The injection device 1 of FIG. 1 is an injection pen that comprises a housing 10 and contains a container 14, e.g. an insulin container, or a receptacle for such a container. The container may contain a drug. A needle 15 can be affixed to the container or the receptacle. The container may be a cartridge and the receptacle may be a cartridge holder. The needle is protected by an inner needle cap 16 and either an outer needle cap 17 or another cap 18. An insulin dose to be ejected from injection device 1 can be set, programmed, or 'dialled in' by turning a dosage knob 12, and a currently programmed or set dose is then displayed via dosage window 13, for instance in multiples of units. The indicia displayed in the window may be provided on a number sleeve or dial sleeve. For example, where the injection device 1 is configured to administer human insulin, the dosage may be displayed in so-called International Units (IU), wherein one IU is the biological equivalent of about 45.5 micrograms of pure crystalline insulin (1/22 mg). Other units may be employed in injection devices for delivering analogue insulin or other medicaments. It should be noted that the selected dose may equally well be displayed differently than as shown in the dosage window 13 in FIG. 1.

The dosage window 13 may be in the form of an aperture in the housing 10, which permits a user to view a limited portion of a dial sleeve assembly that is configured to move when the dial grip 12 is turned, to provide a visual indication of a currently set dose. The dial grip 12 is rotated on a helical path with respect to the housing 10 when setting a dose.

In this example, the dial grip 12 includes one or more formations to facilitate attachment of a data collection device. Especially, the dial grip 12 may be arranged to attach a button module 11 onto the dial grip 12. As an alternative, the dial grip may comprise such a button module of an electronic system.

The injection device 1 may be configured so that turning the dial grip 12 causes a mechanical click sound to provide acoustic feedback to a user. In this embodiment, the dial grip 12 also acts as an injection button. When needle 15 is stuck into a skin portion of a patient, and then dial grip 12 and/or the attached button module 11 is pushed in an axial direction, the insulin dose displayed in display window 13 will be ejected from injection device 1. When the needle 15 of injection device 1 remains for a certain time in the skin portion after the dial grip 12 is pushed, the dose is injected into the patient's body. Ejection of the insulin dose may also cause a mechanical click sound, which may be different from the sounds produced when rotating the dial grip 12 during dialing of the dose.

In this embodiment, during delivery of the insulin dose, the dial grip 12 is returned to its initial position in an axial movement, without rotation, while the dial sleeve assembly is rotated to return to its initial position, e.g. to display a dose of zero units. FIG. 1 shows the injection device 1 in this 0U dialled condition. As noted already, the disclosure is not restricted to insulin but should encompass all drugs in the drug container 14, especially liquid drugs or drug formulations.

Injection device 1 may be used for several injection processes until either the insulin container 14 is empty or the expiration date of the medicament in the injection device 1 (e.g. 28 days after the first use) is reached. In the case of a reusable device, it is possible to replace the insulin container.

Furthermore, before using injection device 1 for the first time, it may be necessary to perform a so-called "prime shot" to remove air from insulin container 14 and needle 15, for instance by selecting two units of insulin and pressing dial grip 12 while holding injection device 1 with the needle 15 upwards. For simplicity of presentation, in the following, it will be assumed that the ejected amounts substantially correspond to the injected doses, so that, for instance the amount of medicament ejected from the injection device 1 is equal to the dose received by the user. Nevertheless, differences (e.g. losses) between the ejected amounts and the injected doses may need to be taken into account.

As explained above, the dial grip 12 also functions as an injection button so that the same component is used for dialling/setting the dose and dispensing/delivering the dose. As an alternative (not shown), a separate injection button may be used which is axially displaceable, at least a limited distance, relative to the dial grip 12 to effect or trigger dose dispensing.

In the following, an electronic system 100 according to the disclosure will be described with respect to exemplary embodiments and with reference to FIG. 4. The electronic system 100 comprises a dose setting and drive mechanism which may be part of an injection device 1 as depicted in FIG. 1 and an electrical power supply 150, e.g. a rechargeable or non-rechargeable battery, as shown in FIG. 4. The electronic system 100 further comprises an electronic control unit 110, e.g. comprising or consisting or being part of a PCBA, configured to control an operation of the electronic system 100 which has a first state and a second state, wherein the electronic system 100 has an increased electrical power consumption in the second state as compared to the first state. The electronic system 100 further comprises an encoding and motion sensing unit 120, e.g. a rotary sensor, and an electrical use detector unit 130 which is operatively connected to the electronic control unit 110 and which is configured to generate at least a first signal which is indicative that the user performs an operation. An example of such an operation is that the user of the injection device and/or the electronic system enters a manual synchronization or pairing mode of the electronic system 100 and/or that a user starts dose dispensing. The electronic system 100 is configured such that it is switched from the first state into the second state by the electronic control unit 110 in response to said first signal. The electronic system further comprises a communication unit 140 for communicating with another device. When the communication unit 140 is active to perform the manual synchronization or pairing mode, the electronic system 100 is in its second state. The PCBA of the electronic control unit 110 may be arranged on and/or in a module chassis 19 of the button module 11 (see FIGS. 2*b* and 3*b*).

Although not explicitly depicted, the electronic system 100 may comprise a, preferably permanent and/or non-volatile, storage or memory unit, which may store data related to the operation of the drug delivery device such as dose history data, for example.

Unless specifically disclosed otherwise in the following, the electronic system 100 may have the functions and may be arranged and/or designed as described in unpublished EP20315066.9 and EP20315357.2, the disclosure of which is incorporated herein by reference.

A first embodiment of a switch assembly 20 is depicted in FIGS. 2*a* to 2*e*.

Figure 2A:
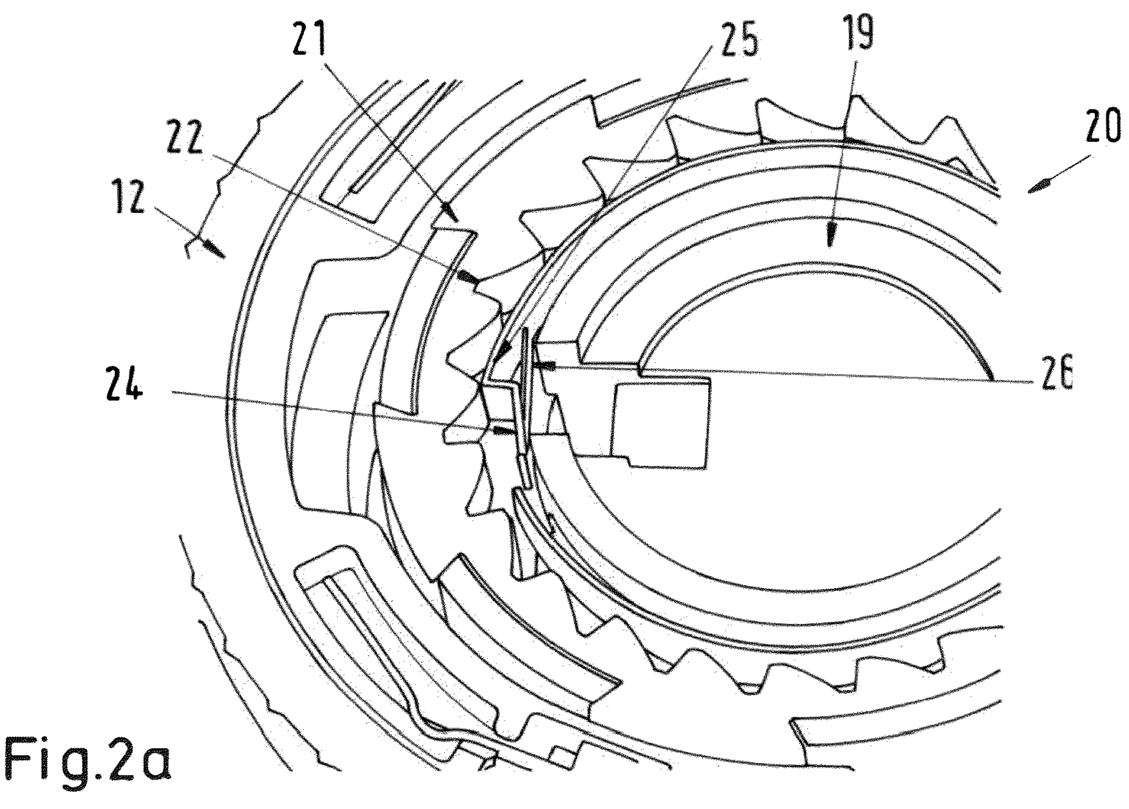
FIG. 2*a* shows a perspective view of a ring of the switch assembly according to a first embodiment of the present disclosure.

In the switch assembly 20, the button module 11 is arranged within the dial grip 12 and comprises the module chassis 19 on which the PCBA of the electronic control unit 110 is located. The module chassis 19 has an outer annular portion held in the dial grip 12 and an inner tubular portion extending into an encoder ring 21 of a dial sleeve assembly. In the depicted embodiment the encoder ring 21 is a separate component part as shown in FIG. 2*a* fixed on the proximal end of a dial sleeve. As an alternative, the encoder ring 21 may be an integral part of a dial sleeve.

The encoder ring 21 comprises a ratchet profile 22 facing radially inwardly of the ring 21. The ratchet profile 22 comprises teeth forming bottom sections and peak sections. A substantially cylindrical portion of the chassis 19 is located in the circular pace defined by the ring 21.

Figure 3A:
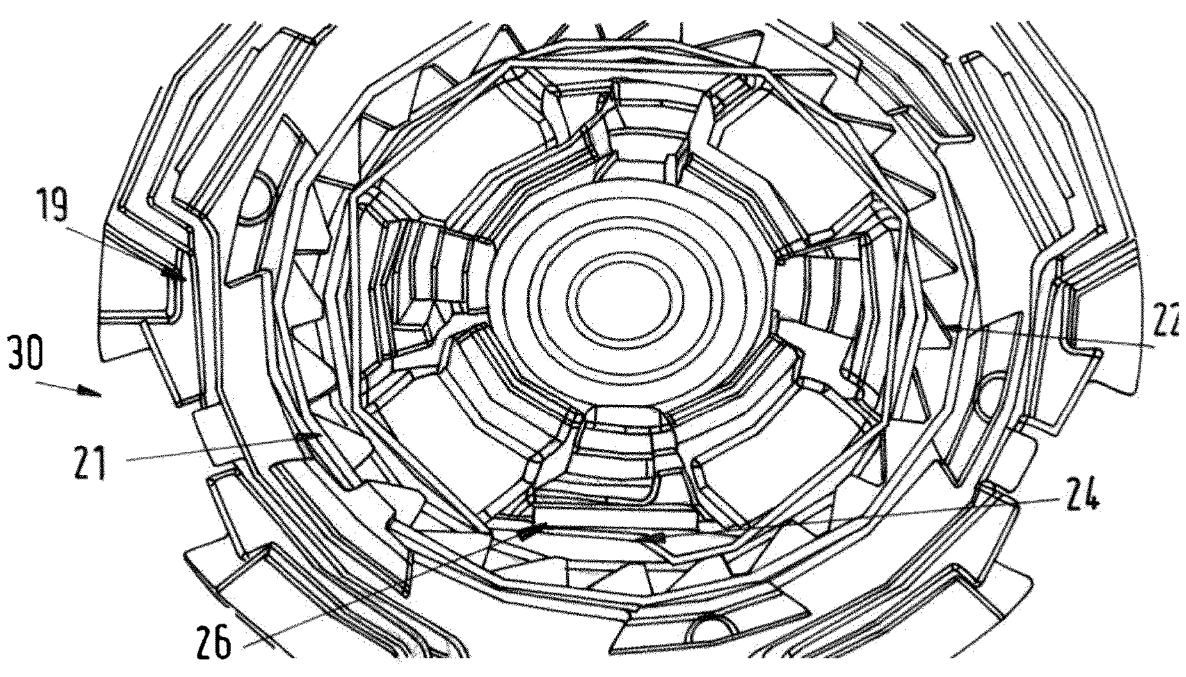
FIG. 3*a* shows a perspective view of a portion the switch assembly according to a second embodiment in the second switch operation mode.
Figure 3B:
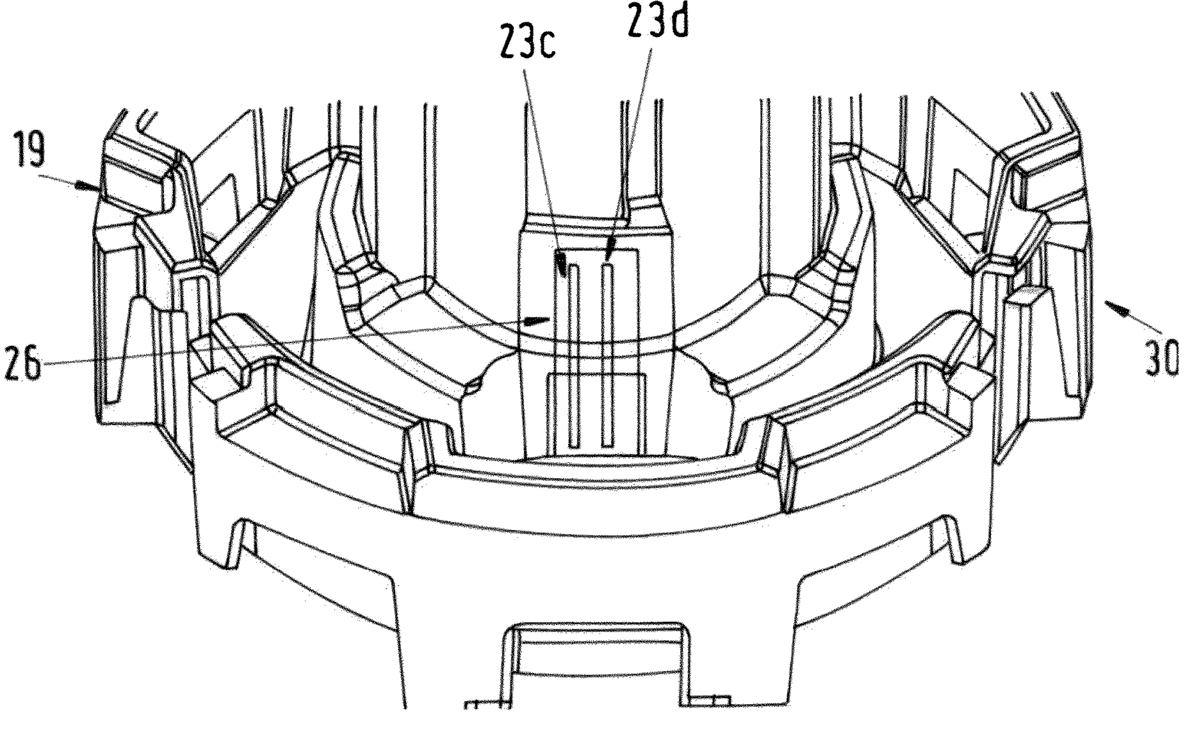
FIG. 3*b* sows a perspective view of a portion of the chassis of FIG. 3*a*.

The distal surface of the PCBA of the electronic control unit 110 comprises a first electrical contact 23*a*, a second electrical contact 23*b*, a third electrical contact 23*c* (FIG. 3*b*) and a fourth electrical contact 23*d* (FIG. 3*b*). In the depicted exemplary embodiment, each of the electrical contacts 23*a*, 23*b* is formed as an elastically deflectable lever having one end which is permanently attached and connected to the PCBA 110 and an opposite free end which may be deflected. The free end of the first lever forming the first contact 23*a* protrudes through an opening in the chassis 19 towards the ring 21 and a dose dial component attached to the ring 21.

Interposed between the ring 21 and the chassis 19 is a substantially annular spring member comprising a free end forming an arm 24 with a detent 25 or protrusion. The detent 25 is adapted to the shape of the ratchet profile 22 such that the detent 25 can enter into the bottom sections and can slide over the peak sections of the ratchet profile 22. The annular spring member is axially and rotationally constrained to the chassis 19 such that, wen the ring 21 and the ratchet profile 22 rotate relative to the chassis 19, the arm maintains its position with respect to the chassis 19.

The third electrical contact 23*c* and the fourth electrical contact 23*d* are arranged on a flexboard section 26 (FIG. 3*b*) of the PCBA 110 extending in the distal direction into the space between the ring 21 and the chassis 19. On this flexboard section 26, the third electrical contact 23*c* and the fourth electrical contact 23*d* are arranged side by side but isolated from each other.

Figure 2B:
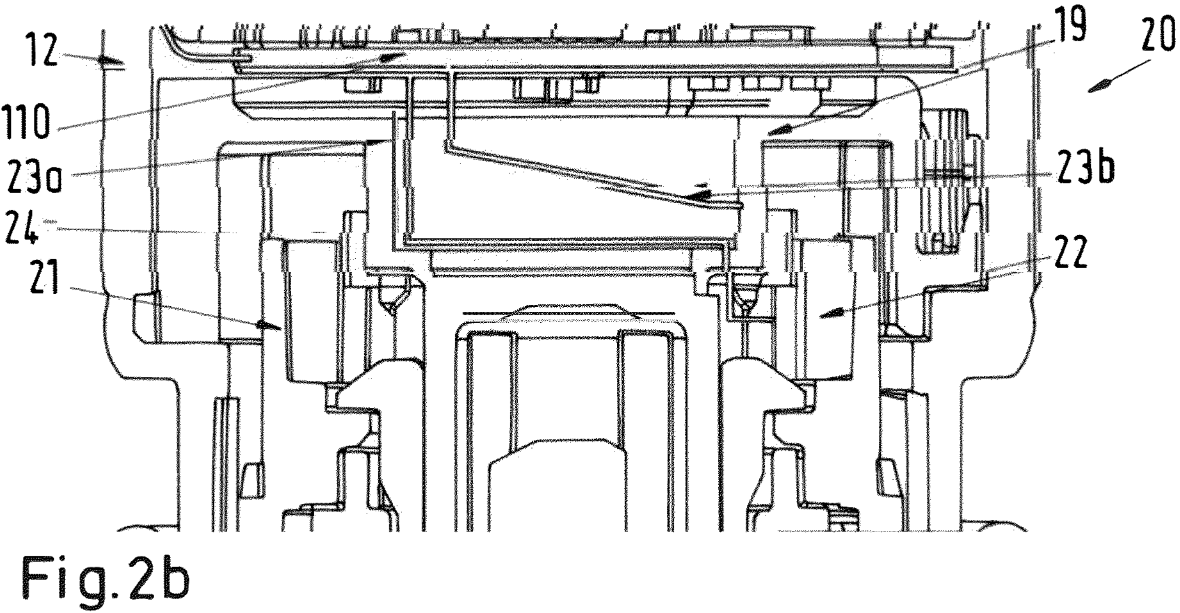
FIG. 2*b* shows a sectional view of the switch assembly according to the first embodiment in a default state.

In a default state of the drug delivery device, i.e. when the drug delivery device is not operated or manipulated by a user, the chassis 19, the ring 21, the arm 24 and the levers are arranged in a state as depicted in FIG. 2*b*. In this a default state the axial switch and the rotary switch of the switch assembly 20 are both open as will be explained in the following.

In the embodiment depicted in the Figures, in the default position, the first electrical contact 23*a* and the second electrical contact 23*b* are spaced from each other such that a circuit between the first electrical contact 23*a* and the second electrical contact 23*b* is open. Further, the third electrical contact 23*c* and the fourth electrical contact 23*d* are isolated from each other and spaced from the arm 24 such that a circuit between the third electrical contact 23*c* and the fourth electrical contact 23*d* is open During dose setting, i.e. when a user selects a higher or lower dose to be dispensed from the drug delivery device 1, the dial grip 12 is rotated by a user with respect to the housing 10.

This causes the simultaneous rotation of the chassis 19 and the encoder ring 21 which are rotationally coupled to each other in the dose setting mode of the drug delivery device 1 via a clutch (not shown) of the dose setting and drive mechanism. Due to the simultaneous rotational movement of the chassis 19 and the encoder ring 21, the relative arrangement of the chassis 19, the ring 21 and the levers and the arm with respect to each other remains the same as in the default state depicted in FIG. 2*b*. During dose setting the dial grip 12 with the chassis 19 and the encoder ring 21 travel on a helical path thereby winding out of the housing 10 as of the selected dose is increased.

Figure 2C:
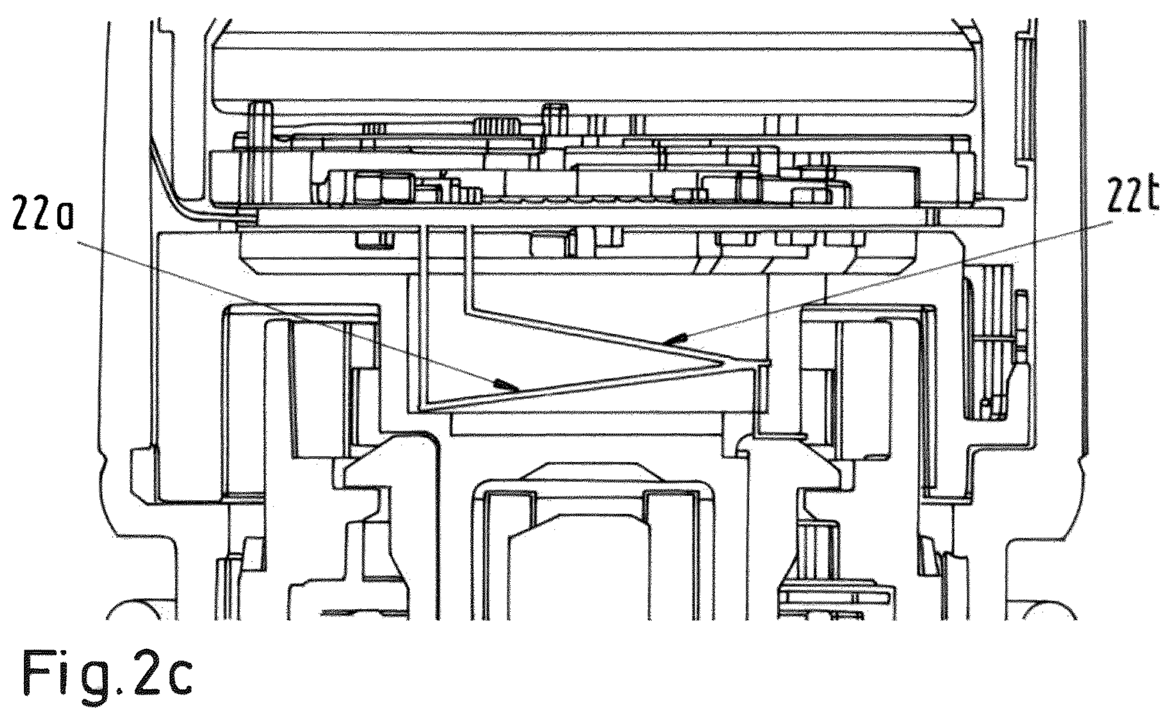
FIG. 2*c* shows a sectional view of the switch assembly according to the first embodiment in the first switch operation mode.
Figure 2D:
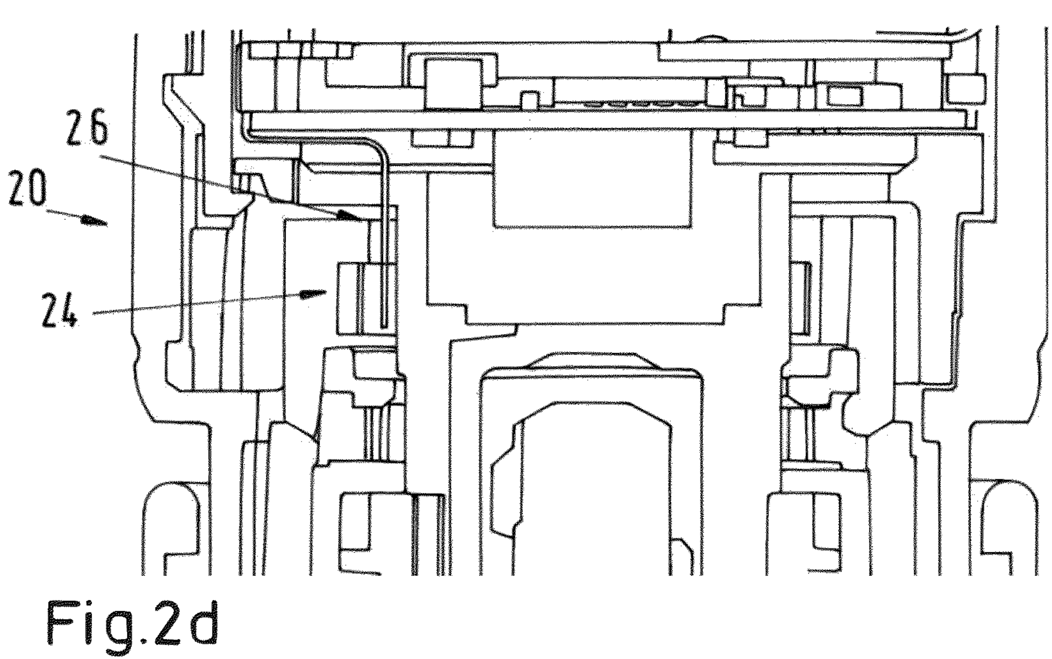
FIG. 2*d* shows a further sectional view of the switch assembly according to the first embodiment in the first switch operation mode.
Figure 2E:
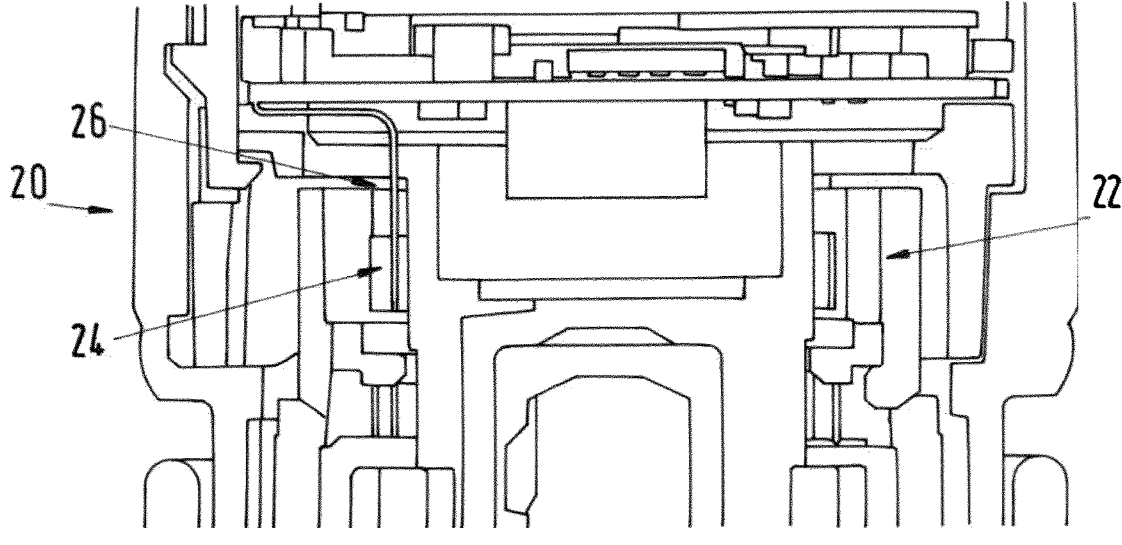
FIG. 2*e* shows a sectional view of the switch assembly according to the first embodiment in the second switch operation mode.

With the dose dialled, a user may start dose dispensing by axially pushing on the proximal end of the dial grip 12. This causes disengagement of the clutch to rotationally decouple the chassis 19 and the encoder ring 21 and causes rotationally coupling the dial grip 12 with the chassis 19 to the housing 10 of the drug delivery device 1. This axial movement includes a limited relative axial movement of the chassis 19 with respect to the encoder ring 21. FIG. 2*c* shows the switch assembly 20 after this limited relative axial movement.

Due to this limited axial movement of the chassis 19 with respect to the encoder ring 21, the first lever with first electrical contact 23*a* abuts a component part coupled to the ring 21 and the free end of the first lever is, thus, deflected proximally (upwards in the Figures). The second lever of the second electrical contact 23*b* remains in its position. The relative movement of the levers causes the levers to abut to each other, thereby closing a circuit by connecting the first electrical contact 23*a* and the second electrical contact 23*b*.

The mere axial movement does not change the position of the arm 24 with respect to the third electrical contact 23*c* and the fourth electrical contact 23*d*. Thus, the rotary switch remains open.

Closing the axial switch of the switch assembly 20 may not only occur during this transition from the dose setting operation to the dose delivery operation of the drug delivery device 1 but may also occur when the dial grip 12, and thus the chassis 19, is pressed to move axially with respect to the encoder ring 21 in a 0U dialled condition of the drug delivery device 1, i.e. prior to dose setting.

This first switch operation mode is preferably used to wake up the communication unit 140, i.e. to switch the communication unit 140 from a sleeping mode into an operation mode inducing the communication unit 140 to initiate a manual synchronisation and/or a pairing with another device. This may occur by means of the electronic control unit 110 in response to the signal generated by closing the axial switch between the levers forming the first contact 23*a* and the second contact 23*b*.

Further depression of the dial grip 12 causes of the dial grip 12 with the chassis 19 to be pushed axially back into the housing 10 while the encoder ring 21 rotates back into the housing 10 along the helical path. In other words, dose dispensing causes a relative rotational movement of the encoder ring 21 with respect to the chassis 19. During this rotational movement the first and second contacts 23*a*, 23*b* remain connected. However, during this rotation the rotary switch changes between the open state in which the arm 24 is not in contact with the flexboard section 26 carrying the third electrical contact 23*c* and the fourth electrical contact 23*d* and the closed state in which the arm 24 is deflected radially inwards towards the flexboard section 26, thereby connecting the third electrical contact 23*c* and the fourth electrical contact 23*d* via the arm 24. As the ring 21 rotates relative to the chassis 19, the detent 25 of the arm is alternately in engagement with a bottom section of the ratchet profile 22, thereby opening the rotary switch, or in engagement with a peak section of the ratchet profile 22, thereby closing the rotary switch by deflecting the arm 24 to bridge the third electrical contact 23*c* and the fourth electrical contact 23*d*. This constitutes a second switch operation mode of the switch assembly 20. The detent 25 snapping back into the bottom sections of the ratchet profile 22 during this dose dispensing operation may generate a tactile and/or audible feedback to a user.

The electronic system is preferably configured such that the rotary sensor 120 is switched from a sleeping mode into an operation mode inducing the rotary sensor 120 to initiate a motion detection upon closing the electrical connection between the third electrical contact 23*c* and the fourth electrical contact 23*d* via the arm 24 during this second switch operation mode. This may occur by means of the electronic control unit 110 in response to the signal generated by alternately closing the rotary switch. The axial switch remains engaged continuously throughout the rotational motion of the encoder ring 21.

The axial switch and the rotational switch of the switch assembly 20 both open as the user releases the dial grip 12 which causes the above described actions to be successively reversed.

A second embodiment of a switch assembly 30 is depicted in FIGS. 3*a* to 3*b*.

In the switch assembly 30, the arrangement of the button module 11, the dial grip 12 and the module chassis 19 with the PCBA of the electronic control unit 110 is as well as the arrangement of an encoder ring 21 with the ratchet profile 22 and the arm 24 is identical to the switch assembly 20. However, the levers forming the first and second contacts 23*a*, 23*b* are removed from the distal surface of the PCBA 110 to the proximal surface of the PCBA 110 (not shown). An axial switch is formed at or near the proximal end of the dial grip 12.

It will be understood that the operation of the switch assembly 30 is substantially the same as described above for the switch assembly 20. In other words, the axial switch and the rotary switch are both open in the default state and during dose setting.

Further, while the rotary switch 23*c*, 23*d*, 24 remains open, the axial switch is closed during transition from the dose setting operation to the dose delivery operation of the drug delivery device 1 or when the dial grip 12, and thus the chassis 19, is pressed to move axially with respect to the encoder ring 21 in a 0U dialled condition of the drug delivery device 1, i.e. prior to dose setting. This first switch operation mode is preferably used to wake up the communication unit 140, i.e. to switch the communication unit 140 from a sleeping mode into an operation mode inducing the communication unit 140 to initiate a manual synchronisation and/or a pairing with another device.

Still further, while the axial switch remains closed, the rotary switch alternately opens and closes during dose delivery operation. The electronic system is preferably configured such that the rotary sensor 120 is switched from a sleeping mode into an operation mode inducing the rotary sensor 120 to initiate a motion detection upon closing the electrical connection between the third electrical contact 23*c* and the fourth electrical contact 23*d* during this second switch operation mode.

Although described mainly with respect to a drug delivery device having a similar working principle as the device disclosed in EP 2 890 435, the electronic system is applicable to any other type of drug delivery device having component parts performing a relative axial and/or rotational movement in defined conditions or states.

REFERENCE NUMERALS

1 device
10 housing
11 button module
12 dial grip
13 dosage window
14 container/container receptacle
15 needle
16 inner needle cap
17 outer needle cap
18 cap
19 module chassis
20 switch assembly
21 encoder ring
22 ratchet profile
23*a*-*d* electrical contact
24 arm
25 detent
26 flexboard section
30 switch assembly
100 electronic system
110 electronic control unit (PCBA)
120 encoding and motion sensing unit
130 use detection unit
140 communication unit
150 electrical power supply

The invention claimed is:

1. A switch assembly for an electronic system of a drug delivery device, the switch assembly comprising:

a chassis supporting a printed circuit board assembly (PCBA) comprising at least a first electrical contact, a second electrical contact, a third electrical contact and a fourth electrical contact;

a ring having an annular ratchet profile;

wherein the chassis moves axially relative to the ring from a first axial position to a second axial position during a first switch operation mode, and wherein the chassis and the ring are configured such that the ring rotates relative to the chassis during a second switch operation mode, wherein the first electrical contact and the second electrical contact are arranged such that upon axial movement of the chassis towards the ring during the first switch operation mode, an electrical connection between the first electrical contact and the second electrical contact is closed, and wherein an elastically deformable arm is radially interposed between the annular ratchet profile of the ring and the chassis, is axially and rotationally constrained to the chassis and is guided on the annular ratchet profile such that the arm at least during the second switch operation mode elastically deforms in a radial direction towards the chassis thereby alternately opening and closing an electrical connection between the third electrical contact and the fourth electrical contact via the arm.

2. The switch assembly of claim 1, wherein the arm comprises a detent or protrusion adapted to engage the annular ratchet profile of the ring.

3. The switch assembly of claim 1, wherein the arm is part of a substantially annular conductive spring member which is biased into abutment with the annular ratchet profile of the ring and which can be at least partially deflected radially inwards into an annular space between the ring and the chassis.

4. The switch assembly of claim 1, wherein third electrical contact and the fourth electrical contact are provided on a flexible flap or a flexboard section of the PCBA which extends distally from the PCBA to a position between the ring and the chassis.

5. The switch assembly of claim 4, wherein the arm alternates between contacting bottom sections and peak sections of the annular ratchet profile and thereby elastically deflects to connect with and disconnect from the third electrical contact and the fourth electrical contact during the second switch operation mode.

6. The switch assembly of claim 1, wherein the first electrical contact is a first lever having one end attached to the PCBA and an opposite free end, wherein the second electrical contact is a second lever having one end attached to the PCBA and an opposite free end, and wherein the free ends of the levers are arranged such that upon axial movement of the chassis towards the ring during the first switch operation mode, an electrical connection between the first electrical contact and the second electrical contact is closed by deflecting at least the first lever with respect to the second lever.

7. The switch assembly of claim 6, wherein the first lever extends through the chassis with its free end protruding out of the chassis into a position in which upon axial movement of the chassis towards the ring during the first switch operation mode, the ring or a component part connected to the ring deflects the first lever.

8. The switch assembly of claim 6, wherein the first lever and the second lever are located in a space formed in the chassis radially inside the ring.

9. The switch assembly of claim 1, further comprising a housing and a dial grip, wherein axial movement of the chassis towards the ring during the first switch operation mode is caused by axial displacement of at least a portion of the dial grip with respect to the housing which closes a gap between the first electrical contact and the second electrical contact.

10. The switch assembly of claim 9, wherein the first electrical contact and the second electrical contact are arranged on a proximal side of the PCBA facing away from the ring.

11. The switch assembly of claim 1, wherein the chassis is closer to the ring in the first axial position than in the second axial position.

12. The switch assembly of claim 1, wherein the first switch operation mode occurs during a transition from the dose setting operation to the dose delivery operation of the drug delivery device or when the chassis is pressed in a 0U dialled condition of the drug delivery device.

13. The switch assembly of claim 1, wherein the second switch operation mode occurs during the dose delivery operation of the drug delivery device.

* * * * *